(12) United States Patent
Ensign

(10) Patent No.: US 7,828,829 B2
(45) Date of Patent: Nov. 9, 2010

(54) LOW TOP BONE FIXATION SYSTEM AND METHOD FOR USING THE SAME

(75) Inventor: Michael D. Ensign, Salt Lake City, UT (US)

(73) Assignee: Pioneer Surgical Technology Inc., Marquette, MI (US)

( * ) Notice: Subject to any disclaimer, the term of this patent is extended or adjusted under 35 U.S.C. 154(b) by 640 days.

(21) Appl. No.: 11/726,868

(22) Filed: Mar. 22, 2007

(65) Prior Publication Data
US 2007/0225711 A1 Sep. 27, 2007

Related U.S. Application Data

(60) Provisional application No. 60/784,674, filed on Mar. 22, 2006.

(51) Int. Cl.
*A61F 2/08* (2006.01)
*A61B 17/86* (2006.01)
*A61B 17/04* (2006.01)

(52) U.S. Cl. .................. 606/305; 606/287; 606/300; 606/306

(58) Field of Classification Search ............... 606/246, 606/264–279, 300–321; 411/104, 337, 340, 411/372.5, 383, 384, 411
See application file for complete search history.

(56) References Cited

U.S. PATENT DOCUMENTS

| | | | |
|---|---|---|---|
| 4,805,602 A | 2/1989 | Puno et al. | |
| 4,946,458 A | 8/1990 | Harms et al. | |
| 4,950,269 A | 8/1990 | Gaines, Jr. | |
| 5,042,982 A | 8/1991 | Harms et al. | |
| 5,120,171 A | 6/1992 | Lasner | |
| 5,176,680 A | 1/1993 | Vignaud et al. | |
| 5,207,678 A | 5/1993 | Harms et al. | |
| 5,226,766 A | 7/1993 | Lasner | |
| 5,257,993 A | 11/1993 | Asher et al. | |
| 5,261,913 A | 11/1993 | Marnay | |

(Continued)

FOREIGN PATENT DOCUMENTS

DE 10005386 A1 8/2001

(Continued)

*Primary Examiner*—Eduardo C Robert
*Assistant Examiner*—Christina Negrelli
(74) *Attorney, Agent, or Firm*—Fitch, Even, Tabin & Flannery

(57) ABSTRACT

An exemplary tulip assembly configured to be coupled to a head of a bone fixation device includes an inner tulip member including a lower portion configured to couple the head of the bone fixation device and an upper portion including a plurality of flexible protrusions extending from the lower portion. According to one exemplary embodiment the plurality of flexible protrusions are configured to provisionally couple a rod. The exemplary tulip assembly also includes an outer tulip member including a first position and a second position, the first position being configured to enable an expansion of the lower portion of the inner tulip member and the second position being configured to compressibly lock the lower portion of the inner member on the bone fixation device. Moreover, the present exemplary tulip assembly also includes a cap having a generally planar top and at least one locking member extending from the top. Wherein the at least one locking member is configured to compress the flexible protrusions to securely lock the rod within the tulip assembly.

28 Claims, 14 Drawing Sheets

U.S. PATENT DOCUMENTS

| | | | |
|---|---|---|---|
| 5,306,275 | A | 4/1994 | Bryan |
| 5,360,431 | A | 11/1994 | Puno et al. |
| 5,368,594 | A | 11/1994 | Martin et al. |
| 5,385,583 | A | 1/1995 | Cotrel |
| 5,492,442 | A | 2/1996 | Lasner |
| 5,520,690 | A | 5/1996 | Errico et al. |
| 5,545,228 | A | 8/1996 | Kambin |
| 5,549,608 | A | 8/1996 | Errico et al. |
| 5,628,740 | A | 5/1997 | Mullane |
| 5,630,817 | A | 5/1997 | Rokegem et al. |
| 5,669,911 | A | 9/1997 | Errico et al. |
| 5,672,176 | A | 9/1997 | Biedermann et al. |
| 5,681,319 | A | 10/1997 | Biedermann et al. |
| 5,683,392 | A | 11/1997 | Richelsoph et al. |
| 5,690,630 | A | 11/1997 | Errico et al. |
| 5,702,393 | A | 12/1997 | Pfaifer |
| 5,728,098 | A | 3/1998 | Sherman et al. |
| 5,810,819 | A | 9/1998 | Errico et al. |
| 5,817,094 | A | 10/1998 | Errico et al. |
| 5,863,293 | A | 1/1999 | Richelsoph |
| 5,879,350 | A | 3/1999 | Sherman et al. |
| 5,910,142 | A | 6/1999 | Tatar |
| 5,964,760 | A | 10/1999 | Richelsoph |
| 5,989,250 | A | 11/1999 | Wagner et al. |
| 5,997,539 | A | 12/1999 | Errico et al. |
| 6,010,503 | A | 1/2000 | Richelsoph et al. |
| 6,053,917 | A | 4/2000 | Sherman et al. |
| 6,063,090 | A | 5/2000 | Schlapfer |
| 6,132,432 | A | 10/2000 | Richelsoph |
| 6,187,005 | B1 | 2/2001 | Brace et al. |
| 6,254,602 | B1 | 7/2001 | Justis |
| 6,280,442 | B1 | 8/2001 | Barker et al. |
| 6,355,040 | B1 | 3/2002 | Richelsoph et al. |
| 6,371,957 | B1 | 4/2002 | Amrein et al. |
| 6,379,356 | B1 | 4/2002 | Jackson |
| 6,402,752 | B2 | 6/2002 | Schaffler-Wachter et al. |
| 6,451,021 | B1 | 9/2002 | Ralph et al. |
| 6,478,797 | B1 | 11/2002 | Paul |
| 6,485,492 | B1 | 11/2002 | Halm et al. |
| 6,660,004 | B2 | 12/2003 | Barker et al. |
| 6,740,086 | B2 | 5/2004 | Richelsoph |
| 6,755,289 | B2 | 6/2004 | Weiss |
| 6,827,719 | B2 | 12/2004 | Ralph et al. |
| 6,837,889 | B2 | 1/2005 | Shluzas |
| 6,840,940 | B2 | 1/2005 | Ralph et al. |
| 6,918,911 | B2 | 7/2005 | Biedermann et al. |
| 7,022,122 | B2 | 4/2006 | Amrein et al. |
| 7,066,937 | B2 | 6/2006 | Shluzas |
| 7,087,057 | B2 | 8/2006 | Konieczynski et al. |
| 7,090,674 | B2 | 8/2006 | Doubler et al. |
| 7,144,396 | B2 | 12/2006 | Shluzas |
| 7,163,539 | B2 | 1/2007 | Abdelgany et al. |
| 7,198,627 | B2 | 4/2007 | Bagga et al. |
| 7,211,086 | B2 | 5/2007 | Biedermann et al. |
| 2002/0026193 | A1 | 2/2002 | Barker et al. |
| 2002/0082602 | A1 | 6/2002 | Biedermann et al. |
| 2002/0111626 | A1 | 8/2002 | Ralph |
| 2002/0116001 | A1 | 8/2002 | Schafer et al. |
| 2003/0004511 | A1 | 1/2003 | Ferree |
| 2003/0100896 | A1 | 5/2003 | Biedermann et al. |
| 2003/0125741 | A1* | 7/2003 | Biedermann et al. ......... 606/61 |
| 2003/0125742 | A1 | 7/2003 | Yuan et al. |
| 2003/0171755 | A1 | 9/2003 | Moseley et al. |
| 2003/0187433 | A1 | 10/2003 | Lin |
| 2004/0097933 | A1 | 5/2004 | Lourdel et al. |
| 2004/0176766 | A1 | 9/2004 | Shluzas |
| 2004/0193160 | A1 | 9/2004 | Richelsoph |
| 2004/0210216 | A1 | 10/2004 | Farris et al. |
| 2004/0225289 | A1 | 11/2004 | Biedermann et al. |
| 2004/0249380 | A1 | 12/2004 | Glascott |
| 2005/0049588 | A1 | 3/2005 | Jackson |
| 2005/0049589 | A1 | 3/2005 | Jackson |
| 2005/0096659 | A1 | 5/2005 | Freudiger |
| 2005/0113830 | A1 | 5/2005 | Rezach |
| 2005/0119658 | A1 | 6/2005 | Ralph et al. |
| 2005/0154391 | A1 | 7/2005 | Doherty et al. |
| 2005/0187548 | A1 | 8/2005 | Butler et al. |
| 2005/0228385 | A1 | 10/2005 | Iott et al. |
| 2005/0267472 | A1 | 12/2005 | Biedermann et al. |
| 2005/0277924 | A1 | 12/2005 | Roychowdhury |
| 2005/0277927 | A1 | 12/2005 | Guenther et al. |
| 2006/0004357 | A1 | 1/2006 | Lee |
| 2006/0025767 | A1 | 2/2006 | Khalili |
| 2006/0089643 | A1 | 4/2006 | Mujwid |
| 2006/0129149 | A1 | 6/2006 | Lott et al. |
| 2006/0149241 | A1 | 7/2006 | Richelsoph et al. |
| 2006/0149244 | A1 | 7/2006 | Amrein et al. |
| 2006/0155278 | A1 | 7/2006 | Warnick |
| 2006/0161152 | A1 | 7/2006 | Ensign et al. |
| 2006/0161153 | A1 | 7/2006 | Hawkes et al. |
| 2006/0173450 | A1 | 8/2006 | Shibata |
| 2006/0173456 | A1 | 8/2006 | Hawkes et al. |
| 2006/0235389 | A1 | 10/2006 | Albert et al. |
| 2006/0241599 | A1 | 10/2006 | Konieczynski |
| 2006/0241600 | A1 | 10/2006 | Ensign et al. |
| 2006/0276789 | A1 | 12/2006 | Jackson |
| 2006/0276791 | A1 | 12/2006 | Shluzas |
| 2006/0276792 | A1 | 12/2006 | Ensign et al. |
| 2006/0293665 | A1 | 12/2006 | Shluzas |
| 2006/0293666 | A1 | 12/2006 | Matthis et al. |
| 2007/0055241 | A1 | 3/2007 | Matthis et al. |
| 2007/0093817 | A1 | 4/2007 | Barrus et al. |
| 2007/0093826 | A1 | 4/2007 | Hawkes et al. |
| 2007/0093827 | A1 | 4/2007 | Warnick |
| 2008/0045955 | A1 | 2/2008 | Berrevoets et al. |
| 2008/0161859 | A1 | 7/2008 | Nilsson |
| 2008/0177325 | A1 | 7/2008 | Drewry et al. |

FOREIGN PATENT DOCUMENTS

| | | |
|---|---|---|
| EP | 0947174 A2 | 6/1999 |
| EP | 1743584 A1 | 1/2007 |
| EP | 1741396 A1 | 10/2007 |
| WO | 2002054966 A2 | 7/2002 |
| WO | 2004047657 A2 | 6/2004 |
| WO | 2006047711 A2 | 5/2006 |
| WO | 2006072284 A1 | 7/2006 |
| WO | 2006116437 A2 | 11/2006 |
| WO | 2006119271 A2 | 11/2006 |
| WO | 2007040750 A2 | 4/2007 |
| WO | 2007040750 A3 | 4/2007 |
| WO | 2008059507 A1 | 5/2008 |

* cited by examiner

LOW TOP BONE FIXATION SYSTEM AND METHOD FOR USING THE SAME

RELATED APPLICATIONS

This application claims the benefit under 35 U.S.C. §119(e) of U.S. Provisional Patent Application No. 60/784,674 filed Mar. 22, 2006 titled "Low Top Pedicle Screw" which provisional application is incorporated herein by reference in its entirety.

FIELD

The present system and method relate to bone fixation devices. More particularly, the present system and method provide for a low profile screw assembly configured to facilitate the internal fixation of vertebral bodies.

BACKGROUND

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw and a rod-receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Although conventional prior art pedicle screw systems exist, they lack features that enhance and/or benefit newer, minimally invasive surgery (MIS) techniques that are more commonly being used for spinal surgeries. It has been suggested that one possible advantage of an MIS approach is that it can decrease a patient's recovery time.

Conventional pedicle screw systems and even more recently designed pedicle screw systems have several drawbacks. Some of these pedicle screw systems are rather large and bulky, which may result in more tissue damage in and around the surgical site when the pedicle screw system is installed during surgery. Traditional pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

SUMMARY

An exemplary tulip assembly configured to be coupled to a head of a bone fixation device includes an inner tulip member including a lower portion configured to couple the head of the bone fixation device and an upper portion including a plurality of flexible protrusions extending from the lower portion. According to one exemplary embodiment the plurality of flexible protrusions are configured to provisionally couple a rod. The exemplary tulip assembly also includes an outer tulip member including a first position and a second position, the first position being configured to enable an expansion of the lower portion of the inner tulip member and the second position being configured to compressibly lock the lower portion of the inner member on the bone fixation device. Moreover, the present exemplary tulip assembly also includes a cap having a generally planar top and at least one locking member extending from the top. Wherein the at least one locking member is configured to compress the flexible protrusions to securely lock the rod within the tulip assembly.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

Throughout the drawings, identical reference numbers designate similar but not necessarily identical elements.

DETAILED DESCRIPTION

Figure 1A:
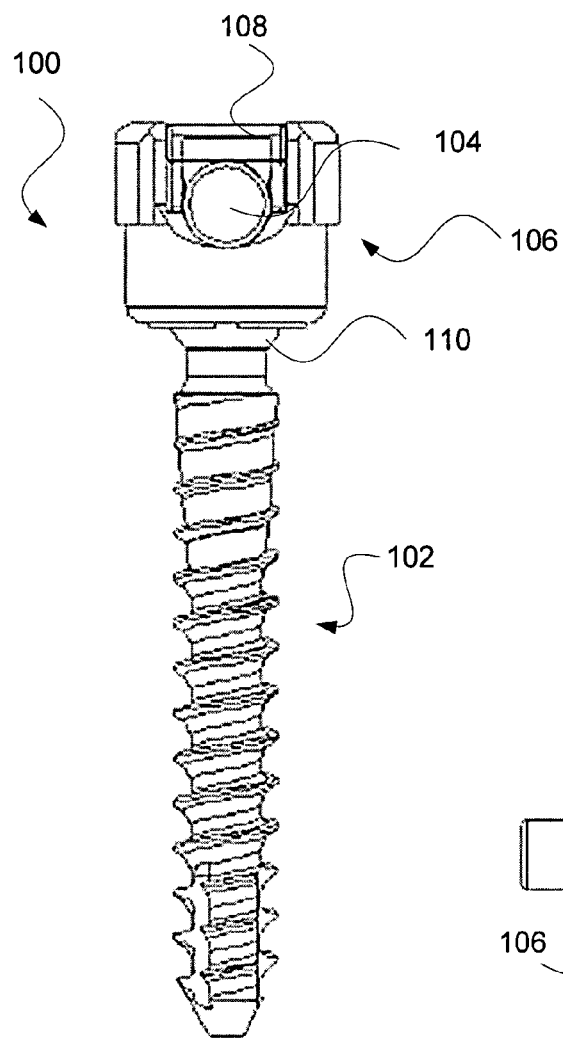
FIGS. 1A and 1B are an axial view and a transverse view, respectively, of an assembled low top pedicle screw system, according to one exemplary embodiment.

The present specification describes a system and a method for separately locking the orientation of a tulip assembly relative to a pedicle screw and locking a positional location of a rod in the tulip assembly. Further, according to one exemplary embodiment, the present specification describes the structure of a tulip assembly configured to be placed on the head of a pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

In addition, pedicle screw systems in accordance with several embodiments of the present system and method advantageously allow a user to initially fix (e.g., lock) the tulip assembly to the pedicle screw at a desired angle either before or after inserting and/or capturing the rod. Initially locking the tulip assembly to the pedicle screw means that at least one of the components of the tulip assembly is manipulated to grip and/or clamp onto the pedicle screw to reduce and/or prevent any translational and/or rotational movement of the tulip assembly relative to the pedicle screw. The ability to initially lock the tulip assembly to the pedicle screw may facilitate the surgeon in performing compression and/or distraction of various spinal and/or bone sections.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Another advantageous feature of at least one embodiment of the present exemplary system and method is that complete tulip assembly that can be coupled to the head portion of the pedicle screw intra-operatively is disclosed. This advantageous tulip assembly may include the aspects or features that enable the tulip assembly to be initially locked onto the head portion of the pedicle screw and then to further receive, capture, and finally lock the rod into the tulip assembly. In one exemplary embodiment, the tulip assembly is initially locked onto the head portion of the pedicle screw after the rod has been received in the tulip assembly. This advantageous tulip assembly may decrease the complexity of the pedicle screw system installation by reducing the installation to essentially a three-step process including, inserting the pedicle screw into bone, initially locking the tulip assembly onto the pedicle screw, which may be accomplished with or without the rod in the tulip assembly, and then capturing and locking the rod into the tulip assembly. In addition to accommodating the new MIS approach to spinal correction and/or fusion, the present exemplary system and method are configured to eliminate instances of cross-threading and/or post-operative tulip splaying, which occurs when the amount of stress/strain in rod, which may be caused by post-operative back flexion forces open the tulip assembly and eventually leads to the disassembly and/or the failure of the pedicle screw system.

In the following description, for purposes of explanation, numerous specific details are set forth in order to provide a thorough understanding of the present system and method for providing a low top pedicle screw coupling system that is capable of separately locking the orientation of a tulip assembly relative to a pedicle screw and a positional location of a rod in the tulip assembly. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Overall Structure

While the present system and method may be practiced by or incorporated into any number of bone fixation systems, the present system and method will be described herein, for ease of explanation only, in the context of a pedicle screw system. Accordingly, the present system and method includes, according to one exemplary embodiment illustrated in FIGS. 1A and 1B, a low top pedicle screw system (100) including a pedicle screw (102), a rod (104), and a coupling assembly (106), herein after referred to as a tulip assembly (106) including a low profile compression cap (108). According to one exemplary embodiment of the present system and method, the tulip assembly (106) is configured to separately lock the orientation of the tulip assembly (106) relative to the pedicle screw (102) and the positional location of the rod (104) in the tulip assembly (106). Operation of the tulip assembly (106) as well as its interaction with both the pedicle screw (102) and the rod (104) will be described in further detail below with reference to the Figures.

Figure 1B:
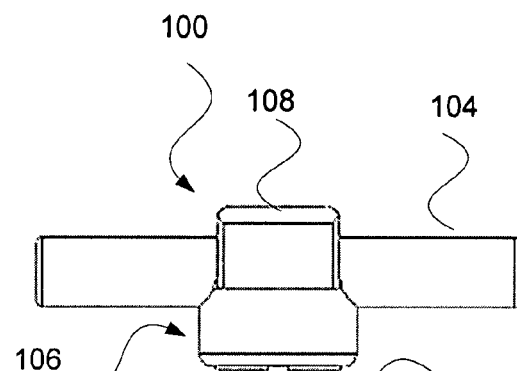
Figure 1B:
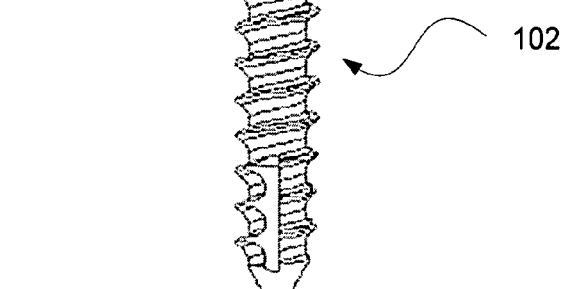

According to one exemplary embodiment, FIGS. 1A and 1B generally show a pedicle screw system (100) comprising a pedicle screw (102), a rod (104), and a coupling assembly (106), hereinafter referred to as a tulip assembly (106). As illustrated in FIG. 1, the pedicle screw system (100) is configured to securely couple the tulip assembly (106) to the head (110) of the pedicle screw (102), thereby locking or fixing the tulip assembly (106) in an angular position relative to the pedicle screw (102). Additionally, as shown in FIGS. 1A and 1B, the present exemplary pedicle screw system (100) is configured to receive a rod (104) and positionally fix the rod (104) in the tulip assembly (106).

Figure 2:
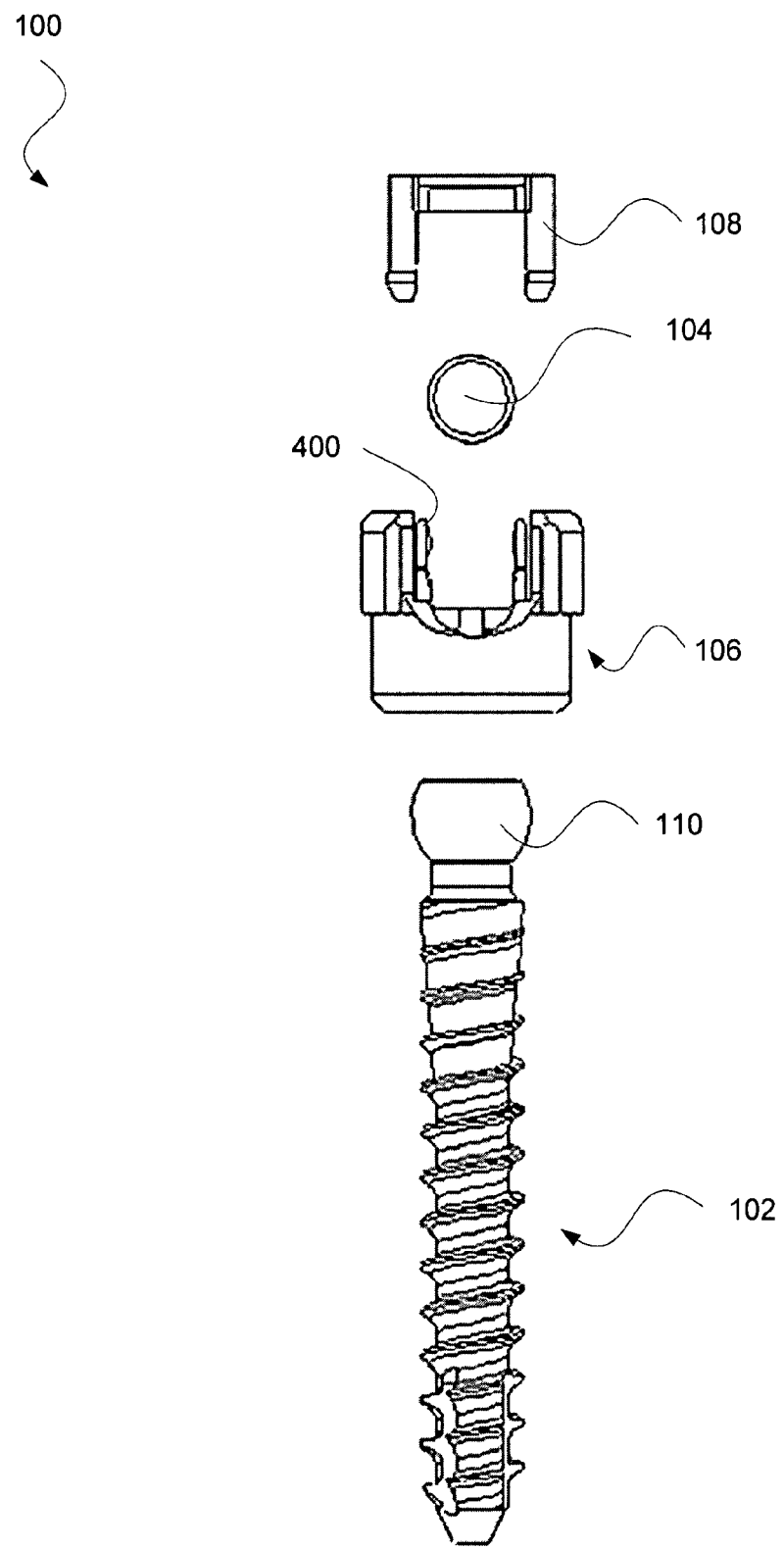
FIG. 2 is an exploded axial view of a low top pedicle screw system, according to one exemplary embodiment.

FIG. 2 illustrates an exploded view of the present low top pedicle screw system (100), according to one exemplary embodiment. As illustrated in FIG. 2, the coupling assembly or tulip assembly (106) of the low top pedicle screw system (100) includes a number of components configured to perform the above-mentioned angular and positional fixing including, but in no way limited to, a tulip assembly (106), an inner tulip member (400), and a compression cap (108). According to one exemplary embodiment, the tulip assembly (106) including the inner tulip member (400) is configured to engage the head portion (110) of the pedicle screw (102), as described in further detail below. Moreover, the tulip assembly (106) in connection with the compression cap (108) is configured to securely couple the rod (104). Detailed descriptions of each component of the present low top pedicle screw system (100) will be described in further detail below, with reference to FIGS. 3 through 9B.

Figure 3:
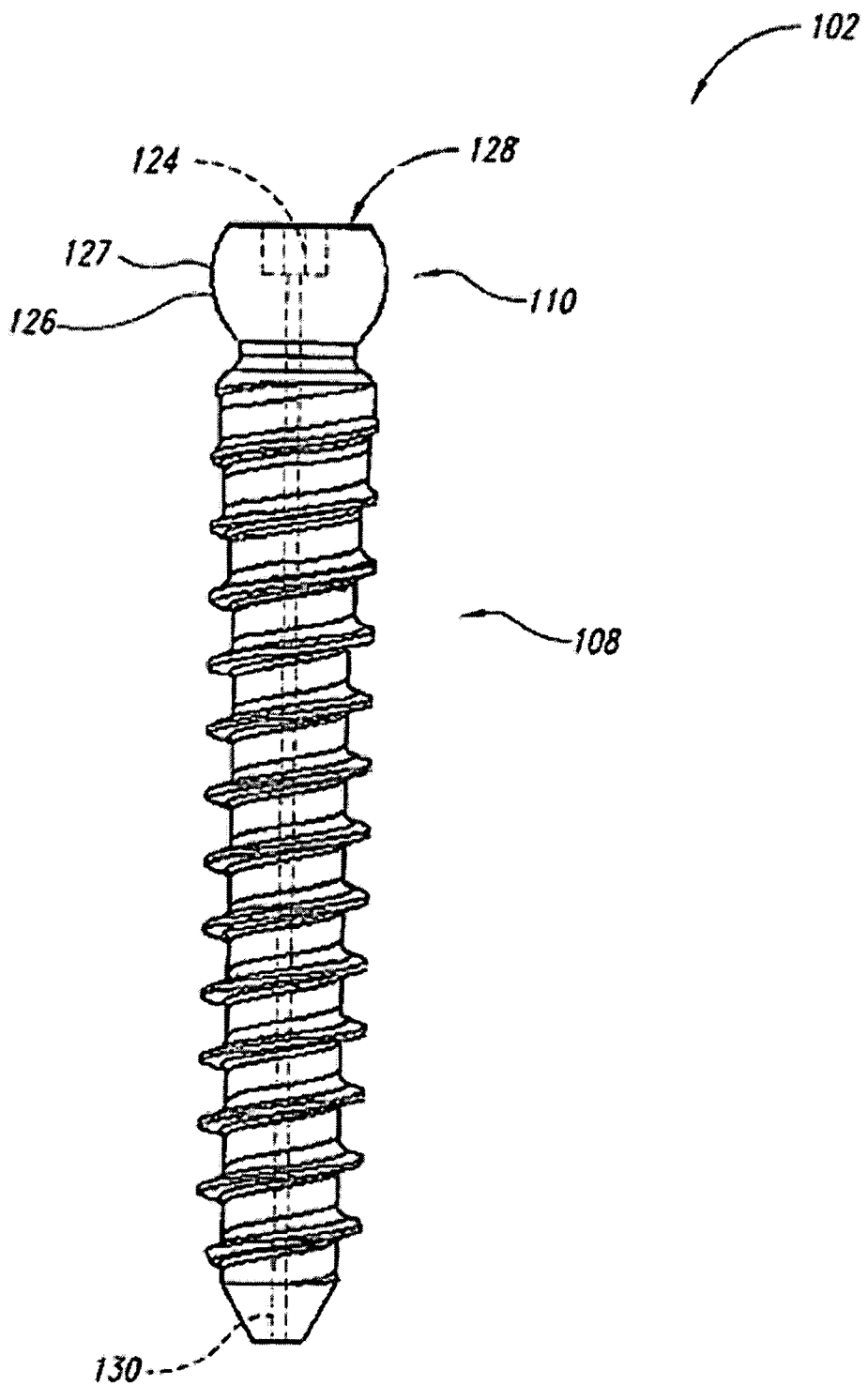
FIG. 3 is a perspective view of a pedicle screw, according to one exemplary embodiment.

FIG. 3 further illustrates the components of a pedicle screw (102), according to one exemplary embodiment. As illustrated in FIG. 3, the pedicle screw (102) includes an elongated, threaded portion (108) and a head portion (110). Although pedicle screws (102) are generally known in the art, the head portions (110) may be of varying configurations depending on what type of tulip assembly (160) is to be coupled to the pedicle screw (102). The head portion (110) of the present exemplary pedicle screw (102) includes a driving feature (124) and a maximum diameter portion (126). The driving feature (124) of the present exemplary pedicle screw (102) permits the screw to be inserted into a pedicle bone and/or other bone. According to one exemplary embodiment, the pedicle bone is a part of a vertebra that connects the lamina with a vertebral body. Additionally, according to the present exemplary embodiment, the driving feature (124) can be used to adjust the pedicle screw (102) prior to or after the tulip assembly (106) is coupled to the pedicle screw (102). In the illustrated embodiment, the head portion (110) of the pedicle screw (102) is coupled to the threaded portion (108) and includes a generally spherical surface (127) with a truncated or flat top surface (128).

In one exemplary embodiment, the pedicle screw (102) is cannulated, which means a channel (130) (shown in dashed lines and extending axially through the pedicle screw (102)) extends through the entire length of the pedicle screw (102). The channel (130) allows the pedicle screw (102) to be maneuvered over and receive a Kirschner wire, commonly referred to as a K-wire (not shown). The K-wire is typically pre-positioned using imaging techniques, for example, fluoroscopy imaging, and then used to provide precise placement of the pedicle screw (102). While the pedicle screw (102) illustrated in FIG. 3 includes a number of components, numerous variations may be made including, but in no way limited to, varying the type of driving feature (124), varying materials, varying dimensions, and the like.

Figure 4:
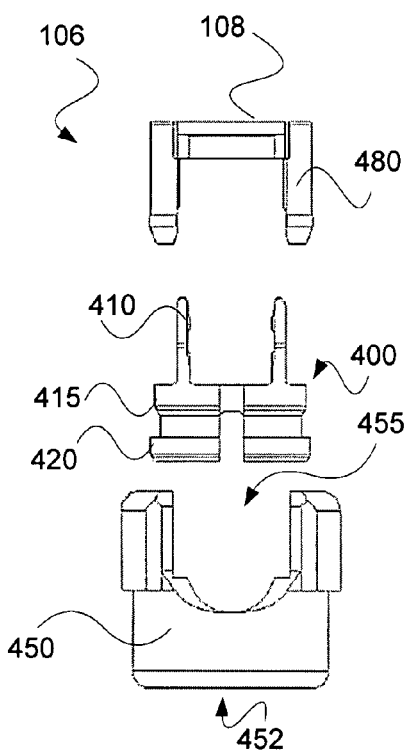
FIG. 4 is an axial exploded view of a tulip assembly of the low top pedicle screw system of FIG. 1, according to one exemplary embodiment.
Figure 5:
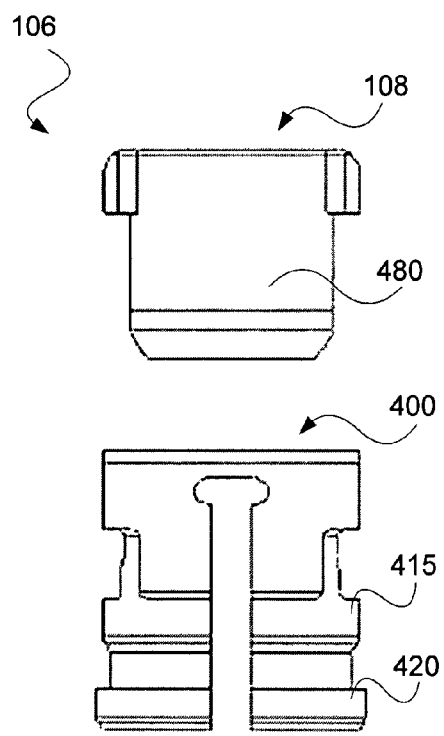
FIG. 5 is a transverse exploded view of a tulip assembly of the low top pedicle screw system of FIG. 1, according to one exemplary embodiment.
Figure 6:
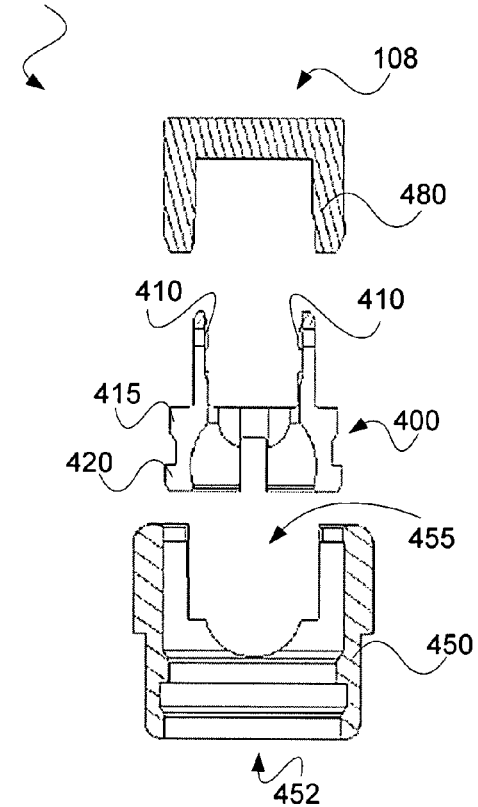
FIG. 6 is an axial exploded cross-sectional side view of the low top pedicle screw system of FIG. 4, according to one exemplary embodiment.

Returning again to FIG. 1, the pedicle screw system includes a tulip assembly (106) configured to separately lock the orientation of the tulip assembly (106) relative to the pedicle screw (102) and the positional location of the rod (104) within the tulip assembly (106). FIGS. 4, 5, and 6 illustrate the various components of the present exemplary tulip assembly (106), according to one exemplary embodiment. FIG. 4 illustrates an exploded view of the present exemplary tulip assembly (106) as viewed from an axial direction of a captured rod (104), while FIG. 5 illustrates an exploded view of the present exemplary tulip assembly (106) as viewed from a transverse direction of a captured rod (104). Furthermore, FIG. 6 provides a cross-sectional axial view of the present exemplary tulip assembly (106). As illustrated in FIGS. 4-6, the present exemplary tulip assembly (106) includes a tulip body (450) substantially housing an inner tulip member (400). Additionally, a thru-bore (452) is defined in the center of the tulip assembly (106) to provide access to the driving feature (124; FIG. 3) of a pedicle screw (102; FIG. 3) and/or a K-wire. The tulip body (450) also defines a rod recess (455) configured to define an ultimate rod position during use.

As shown, the inner tulip member (400) includes a number of functional features including, but in no way limited to a plurality of rod engagement members (410) configured to establish contact points on a received rod. Additionally, a proximal seating feature (415) and a distal seating feature (420) are formed on the outer surface of the inner tulip member (400) in order to interact with the tulip body (450) and selectively capture the head (110; FIG. 3) of a pedicle screw (102; FIG. 3). Furthermore, the compression cap (108) includes a plurality of compression protrusions (480) and other elements that work to provide the above-mentioned ability to separately lock the orientation of the tulip assembly (106) relative to the pedicle screw (102) and lock a rod. Consequently, the exemplary configurations of the tulip body (450), the inner tulip member (400), and the compression cap (108) will each be independently addressed in detail below with reference to FIGS. 7A through 9C.

Figure 7A:
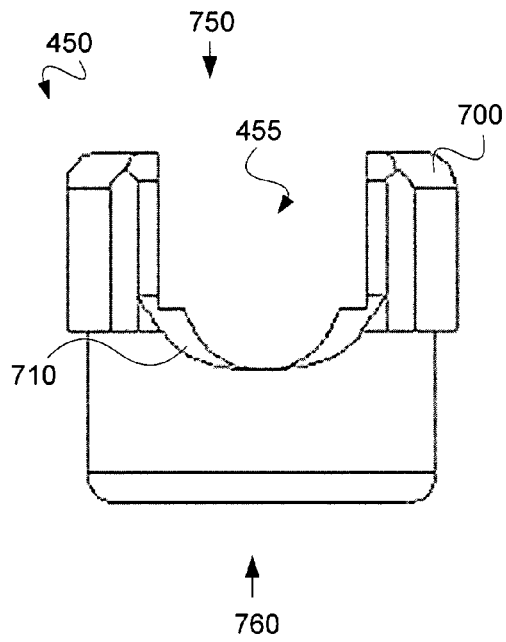
FIGS. 7A-7D are axial, transverse, axial cross-sectional, and cut-away perspective views, respectively, of a tulip body, according to one exemplary embodiment.
Figure 7B:
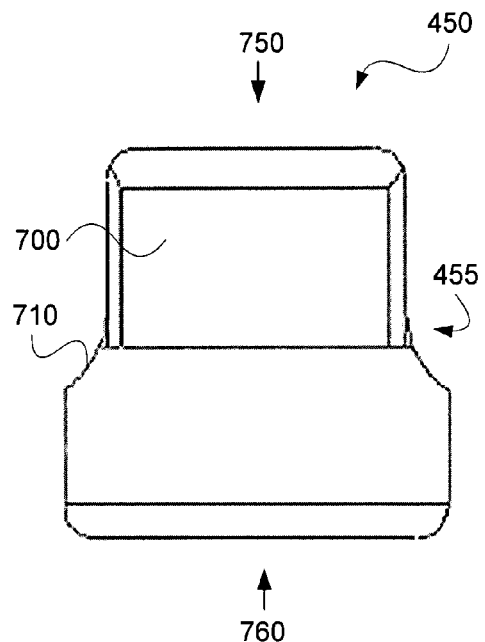
Figure 7C:
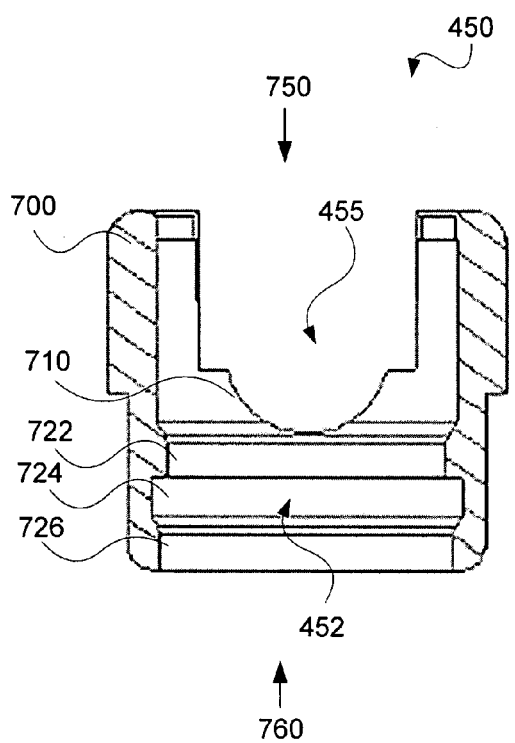
Figure 7D:
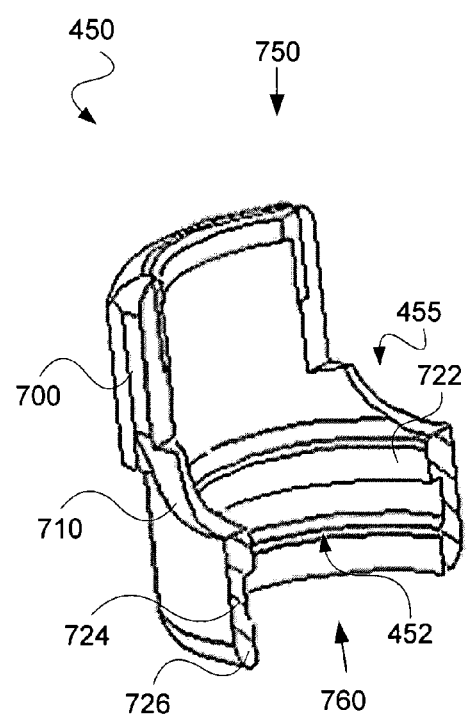

FIG. 7A illustrates an axial side view of a tulip body (450), FIG. 7B illustrates a transverse side view of the tulip body, FIG. 7C illustrates an axial cross-sectional view of the tulip body, and FIG. 7D illustrates a partial cut-away perspective view of the tulip body, according to one exemplary embodiment. As illustrated in FIGS. 7A through 7D, the tulip body (450) includes a number of elements that facilitate reception of a pedicle screw head portion (110; FIG. 3) and the ability to separately lock both the orientation of the tulip assembly (106; FIG. 1) relative to the pedicle screw (102; FIG. 1) and a positional location of a rod (104; FIG. 1) in the tulip assembly. According to one exemplary embodiment illustrated in FIGS. 7A through 7D, the tulip body (450) includes a thru-bore (452), a proximal end (750), a distal end (760), a rod reception recess (455) defined by a plurality of side walls (700), and a number of internal annular features (722, 724, and 726) configured to allow for the selective compression and expansion of an inner tulip member (400; FIG. 4).

According to one exemplary embodiment, the bore (452) is configured to facilitate assembly of the tulip assembly (106; FIG. 4) before being placed onto the head portion of the pedicle screw (102; FIG. 1). In one embodiment, the inner tulip member (400; FIG. 4) of the tulip assembly may be inserted into the tulip body (450) through the bore (452). Additionally, once the tulip assembly (106; FIG. 4) is preoperatively assembled, the bore (452) facilitates reception of the head portion (110; FIG. 3) of the pedicle screw (102; FIG. 3) during the initial coupling of the tulip assembly (106; FIG. 4) to the pedicle screw (110; FIG. 3), as will be described in further detail below.

Continuing with FIGS. 7A through 7D, the tulip body (450) is illustrated as a generally cylindrical member having a plurality of side walls (700) extending toward the proximal end (750) of the tulip body. According to one exemplary embodiment, the plurality of side walls (700) define both the proximal portion of the thru-bore (452) and the rod recess (455) including a rod stop surface (710). As illustrated, the proximal portion of the tulip body (450) is open, allowing for selective reception and retention of a rod (104; FIG. 1), according to one exemplary embodiment. As mentioned, the rod (104; FIG. 1) may be inserted into the tulip body (132) either before or after placement of the tulip assembly (106; FIG. 4) on the head portion (110; FIG. 3) of the pedicle screw (102; FIG. 3). Initial placement of the rod (104; FIG. 1) is received by both the inner tulip member (400; FIG. 4) and the tulip body (450) via the rod recess (455). Consequently, according to one exemplary embodiment, the width of the rod recess (455) may be substantially equal to or greater than the diameter of a desired rod (104; FIG. 1). However, according to other exemplary embodiments, the rod recess (455) may be slightly narrower than the diameter of a desired rod (104; FIG. 1) to allow for a slight interference fit during insertion. Once the rod (104; FIG. 1) is received by the tulip body (450) and the inner tulip member (400; FIG. 4) via the rod recess (455) the lateral motion of the rod is limited by the sidewalls (700) and the vertical position of the rod is limited, at least in part, by the rod stop surface (710).

The present exemplary tulip body (450) also includes a number of elements that allow the relative angular position of the tulip assembly (106; FIG. 4) to be independently established relative to the pedicle screw (102; FIG. 1). Specifically, the internal wall of the tulip body (450) defining the thru-bore (720) can include, according to one exemplary embodiment, a proximal annular compression feature (722), a distal annular compression feature (726) and an annular expansion groove (724). According to one exemplary embodiment, the proximal and distal annular compression features (722, 726) are configured to interact with the proximal seating feature (415; FIG. 4) and the distal seating feature (420; FIG. 4) of the inner tulip member (400; FIG. 4) to compress the head portion (110; FIG. 3) of the pedicle screw (102; FIG. 3), thereby fixing the relative angular position of the tulip assembly (106; FIG. 4) relative to the pedicle screw, as will be described below with reference to FIGS. 10 through 16B. Additionally, according to one exemplary embodiment, the annular expansion groove (724) is configured to permit selective expansion of the inner tulip member (400; FIG. 4) to facilitate the press-on reception of the head portion (110; FIG. 3) of the pedicle screw (102; FIG. 2), as will be described in detail below. While the present figures and description describe the internal compression and expansion features as annular protrusions and recesses, any number of selectively disjointed, or varying protrusions or recesses may be used to allow selective expansion and compression of the present inner tulip member (400; FIG. 4).

Figure 8A:
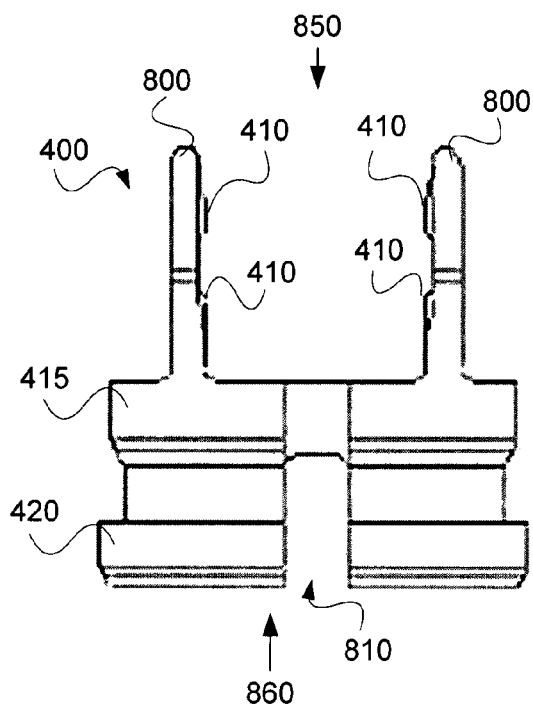
FIGS. 8A-8C are axial, transverse, and cut-away perspective views, respectively, of an inner tulip member, according to one exemplary embodiment.
Figure 8B:
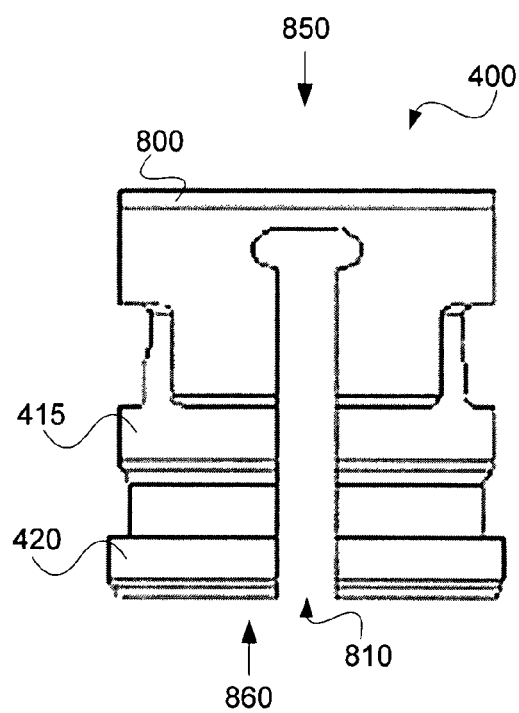
Figure 8C:
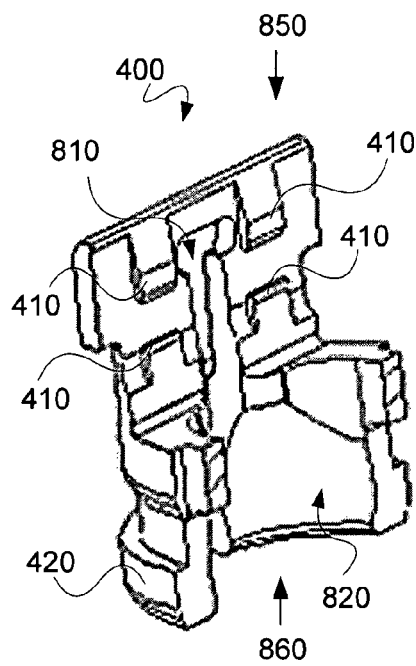

The inner tulip member (400) of the present tulip assembly (106; FIG. 4) is illustrated in FIGS. 8A through 8C. As shown by the side axial view of FIG. 8A, the inner tulip member (400) can generally, according to one exemplary embodiment, include a main body having a proximal end (850) and a distal end (860). As shown, the main body of the inner tulip member (400) includes a plurality of rod retention protrusions (800) extending there from in a proximal direction. According to one exemplary embodiment, the rod retention protrusions (800) include a number of rod engagement members (410) formed on an inner surface of the rod retention protrusions. According to one exemplary embodiment, the rod retention protrusions (800) are spaced apart a proper distance to receive a desired rod (104; FIG. 1) and contact and retain the desired rod at the rod engagement members (410). As shown in FIG. 8A, an expansion gap (810) may be formed in the distal end (860) of the inner tulip member (400) to facilitate expansion and contraction of the rod retention protrusions (800) normal to a received rod. Additionally, as previously mentioned, the inner tulip member (400) can include a proximal seating feature (415) and a distal seating feature (420) configured to selectively interact with the proximal annular compression feature (722; FIG. 7C), the annular expansion gap (724; FIG. 7C), and the distal annular compression feature (726; FIG. 7C) of the tulip body (450; FIG. 7A). According to one exemplary embodiment, the main body, and the rod retention protrusions are sized to be received in the thru bore (452) of the tulip body (450; FIG. 7C) and then be selectively translatable within the tulip body to compress the head portion of a desired pedicle screw (102; FIG. 1), as will be described in more detail below.

Turning now to FIG. 8B, which is a transverse view of the inner tulip member (400), the body of the inner tulip member defines an expansion gap (810) that begins at the distal end (860) of the inner tulip member (400) and extends into the upper rod retention protrusions (800). According to one exemplary embodiment, the large expansion gaps (810) defined in the inner tulip member (400) facilitate expansion of the distal end (860) of the inner tulip member, thereby allowing for reception of a head portion of a desired pedicle screw (102; FIG. 1). As shown in FIG. 8C, the distal end (860) of the inner tulip member (400) defines a head receiving orifice (820) configured to provide a large surface area of contact with a received pedicle screw head. As will be described in further detail below, the aforementioned features of the inner tulip member (400) will work in conjunction with the features of the tulip body (450; FIG. 4) and the compression cap (108; FIG. 4) to selectively fix the position of the present tulip assembly (106; FIG. 4) relative to a pedicle screw and independently receive, capture, and eventually positionally lock a rod (104; FIG. 1) into the tulip assembly. According to one exemplary embodiment, a forced contraction of the distal end (860) of the inner tulip member (400) generates sufficient radial pressure on the head portion (110; FIG. 3) of the pedicle screw (102; FIG. 3) to lock the relative angular position of the tulip body (450; FIG. 1) with respect to the pedicle screw.

Figure 9A:
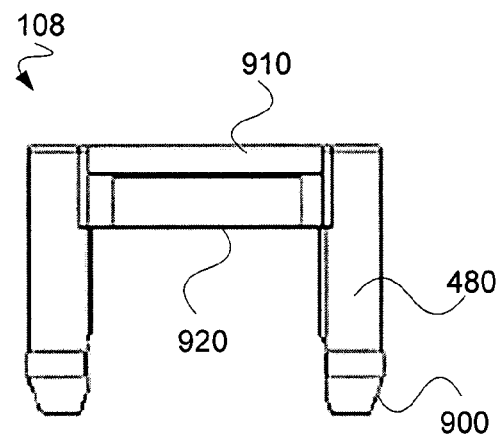
FIGS. 9A-9C are axial, transverse, and cut-away perspective views, respectively, of a compression cap, according to one exemplary embodiment.
Figure 9B:
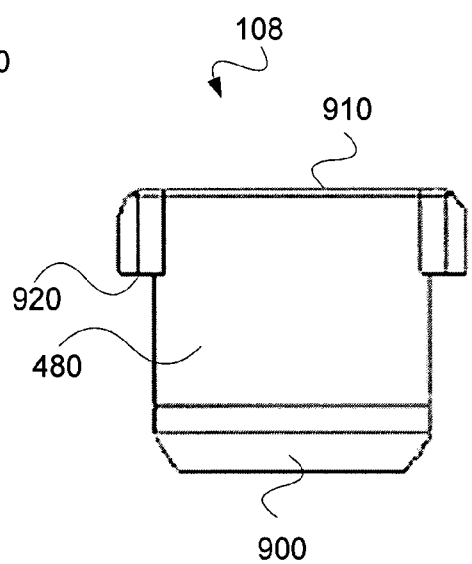
Figure 9C:
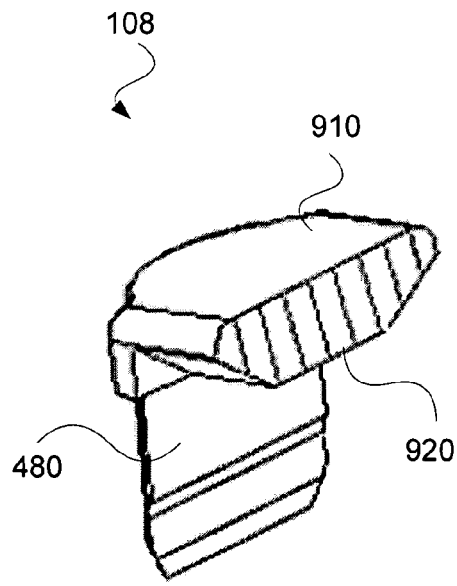

FIGS. 9A through 9C illustrate the compression cap (108) of the present exemplary system and method. According to one exemplary embodiment, the compression cap (108) of the present system and method is designed to provide a low top assembly, while preventing post operative tulip splaying and rod fixation. Particularly, as shown in FIGS. 9A through 9C, the compression cap (108) includes a top surface (910) and a bottom rod mating surface (920). According to one exemplary embodiment, a plurality of compression protrusions (480) extends distally from the bottom rod mating surface (920) at the edges of the compression cap (108). According to one exemplary embodiment, described in further detail below, each of the compression protrusions (480) are configured to be inserted between the rod retention protrusions (800; FIG. 8A) of the inner tulip members (400; FIG. 8A) and the side walls (700; FIG. 7A) of the tulip body (450). According to one exemplary embodiment, forcing the compression protrusions (480) between the rod retention protrusions (800; FIG. 8A) of the inner tulip members (400; FIG. 8A) and the side walls (700; FIG. 7A) of the tulip body (450) both compresses the compression protrusions about a captured rod (104; FIG. 1) and prevents the inner tulip member (400; FIG. 4) from splaying post operatively. As shown in FIGS. 9A and 9B, the most distal portion of the compression protrusions (480) may include an engagement bevel (900) configured to facilitate the insertion of the compression protrusions between the rod retention protrusions (800; FIG. 8A) of the inner tulip members (400; FIG. 8A) and the side walls (700; FIG. 7A) of the tulip body (450). While a number of traditional rod retention systems include anti-splaying mechanisms, they are typically bulky and greatly increase the overall height of the mechanism. In contrast, the present compression cap (108) protects against post operative splaying of the system while minimally impacting the height of the resulting assembly. That is, the only height of the present tulip assembly (106; FIG. 4) above a captured rod when fully assembled is the distance between the rod mating surface (920) and the top surface (910) of the compression cap (108), as illustrated in FIG. 9A.

Further detail of the function and operation of the present tulip assembly (106; FIG. 4) will be described below with reference to FIGS. 10-16B.

Exemplary Implementation and Operation

Figure 10:
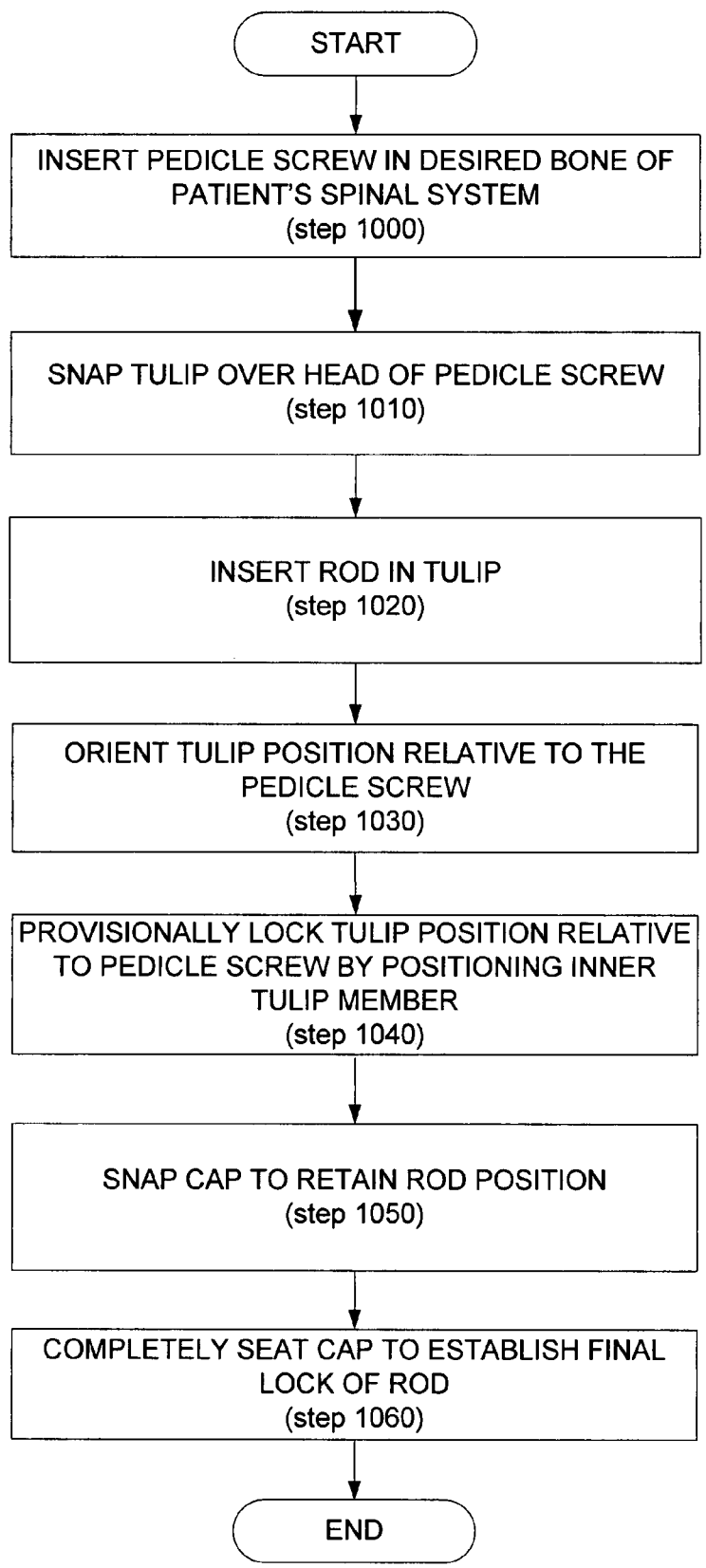
FIG. 10 is a flow chart illustrating a method for securing a low top tulip assembly on a pedicle screw, according to one exemplary embodiment.

FIG. 10 illustrates one method for installing the exemplary low top pedicle screw system (100; FIG. 1), according to one exemplary embodiment. As illustrated in FIG. 10, the present exemplary method for installing the low top pedicle screw system (100; FIG. 1) includes inserting one or more pedicle screws in a patient's spinal system (step 1000). Once the one or more pedicle screws are inserted in a patient's spinal system, the tulip assembly (106; FIG. 1) is installed over the head of the pedicle screw (step 1010). With the tulip assembly snapped over the head of the pedicle screw, a rod may be inserted into the rod recess of the tulip (step 1020) and the relative position of the tulip assembly may be oriented as desired relative to the pedicle screw (step 1030). When the desired orientation is established, the tulip assembly position relative to the pedicle screw may be provisionally locked by positioning the inner tulip member (step 1040). With the tulip position relative to the pedicle screw established due to the positioning of the inner tulip member, the compression cap may be snapped into the assembly to retain the rod (step 1050) followed by a complete insertion of the compression cap for a final lock of the rod (step 1060). Further details of each step of the present exemplary method will be provided below with reference to FIGS. 11A through 16B.

As illustrated in FIG. 10, the first step of the exemplary method is to insert one or more pedicle screws in a patient's spinal system (step 1000) corresponding to a desired number of pedicle screw systems (100; FIG. 1). The placement and/or number of pedicle screw systems (100; FIG. 1) to be used in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example.

Figure 11A:
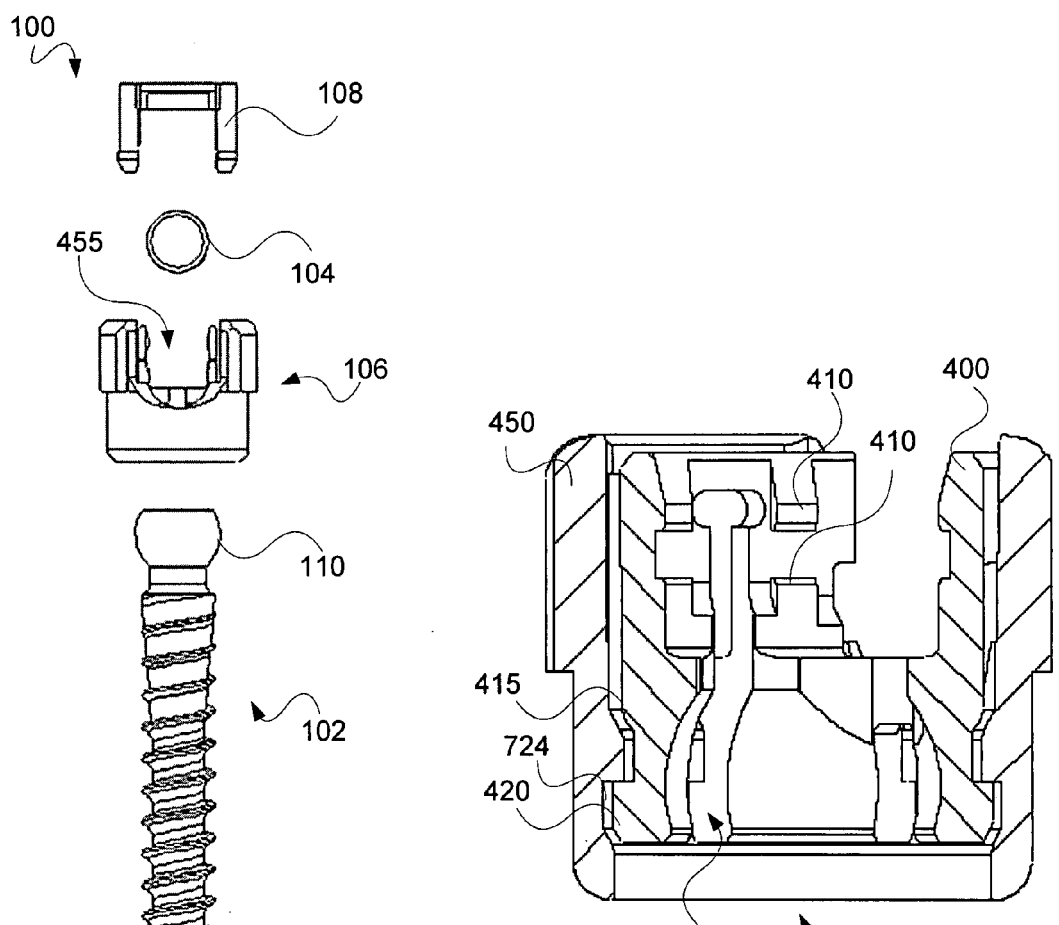
FIGS. 11A and 11B are an axial view and a cross-sectional side view, respectively, of the components of a low top pedicle screw system prior to assembly, according to one exemplary embodiment.
Figure 11B:
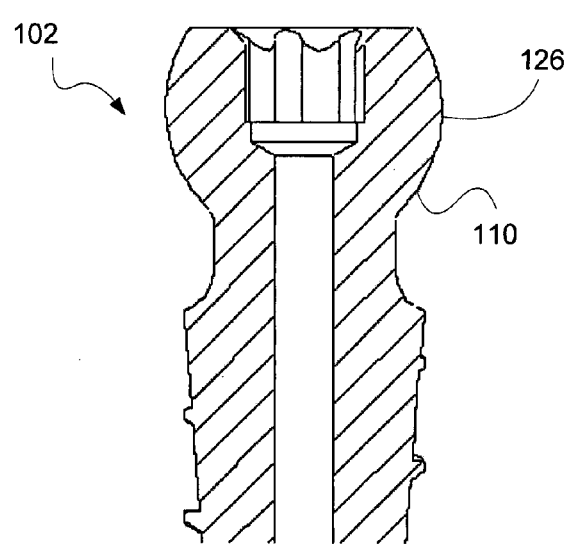

With the one or more pedicle screws inserted into a patient's spinal system (step 1000), the tulip assembly may be snapped over the head of a previously inserted pedicle screw (step 1010). FIGS. 11A and 11B illustrate the exemplary components prior to installation on an inserted pedicle screw (102). As illustrated, the inner tulip member (400) is in an up position aligning the distal seating feature (420) of the inner tulip member (400) with the annular expansion groove (724) of the tulip body (450). According to one exemplary embodiment, this configuration allows for the expansion of the head receiving orifice (820), thereby facilitating the reception of the head portion (110) of the pedicle screw (102). More specifically, according to one exemplary embodiment, the alignment of the distal seating feature (420) of the inner tulip member (400) with the annular expansion groove (724) of the tulip body (450) allows the head receiving orifice (820) to expand to a diameter larger than the max diameter (126) of the pedicle screw head (110).

Figure 12A:
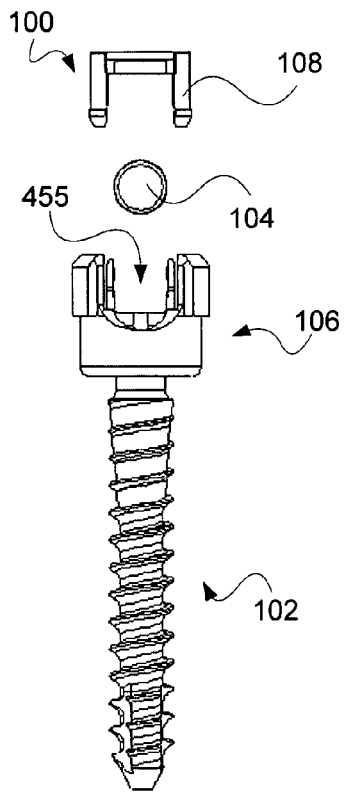
FIGS. 12A and 12B are an axial view and a cross-sectional side view, respectively, of the components of the low top pedicle screw system of FIG. 10 with the tulip assembly coupled to a head of a pedicle screw, according to one exemplary embodiment.
Figure 12B:
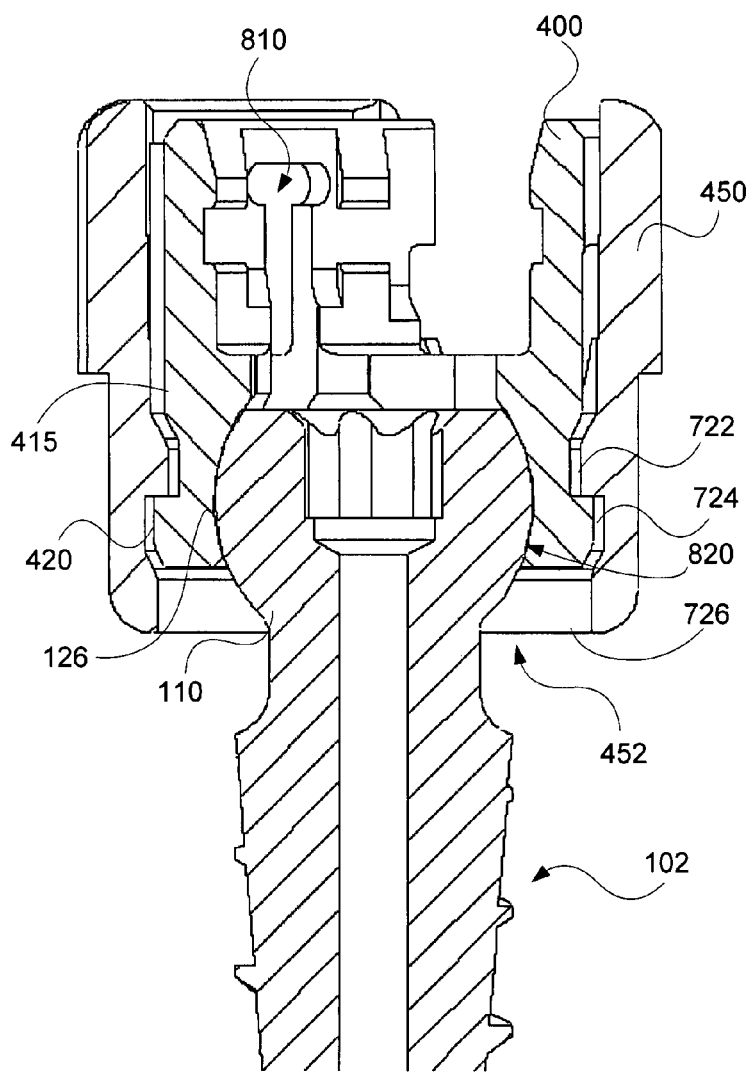

With the tulip assembly (106) in position, the screw head is snapped into the head receiving orifice (820), as illustrated in FIGS. 12A and 12B. According to one exemplary embodiment, the tulip assembly (106) may be intra-operatively (i.e., during surgery) coupled to the head portion (110) of the pedicle screw (102) and may be maneuverable to achieve a desired placement, orientation, and/or angular position of the tulip assembly (106) relative to the pedicle screw (102).

According to one exemplary embodiment, when the tulip assembly (106) is snapped onto the head portion (110) of the pedicle screw (102), the head portion (110) of the pedicle screw (102) passes through the thru-bore (452) and engages the lower portion of the inner tulip member (400). As the tulip assembly (106) is pushed onto the head portion (110) of the pedicle screw (102), the lower portion of the inner tulip member (400) expands, due in part to the expansion gap (810; FIG. 8B) and snaps onto the head portion (110). The annular expansion groove (724) in the lower portion of the tulip body (450) permits the expansion and contraction of the inner tulip member (400). Once the head portion (110) of the pedicle screw (102) is received in the head receiving orifice (820), the inner tulip member (400) compresses about the head portion of the pedicle screw. At this point of the installation method, the tulip assembly (106) may be rotationally coupled to the head portion (110) of the pedicle screw (102).

Figure 13A:
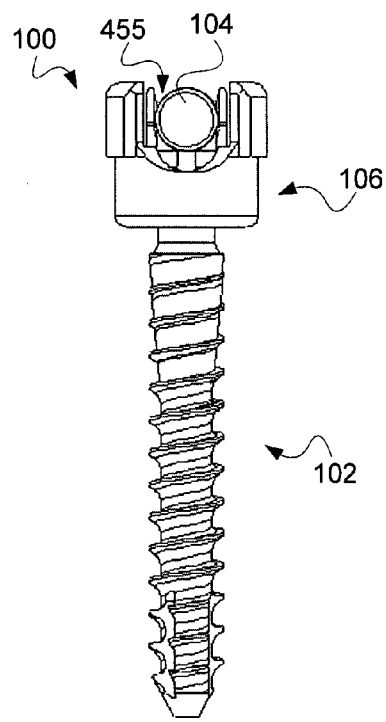
FIGS. 13A and 13B are an axial view and a cross-sectional side view, respectively, of the components of the low top pedicle screw system of FIG. 10 as a rod is snapped into the internal tulip member, according to one exemplary embodiment.
Figure 13B:
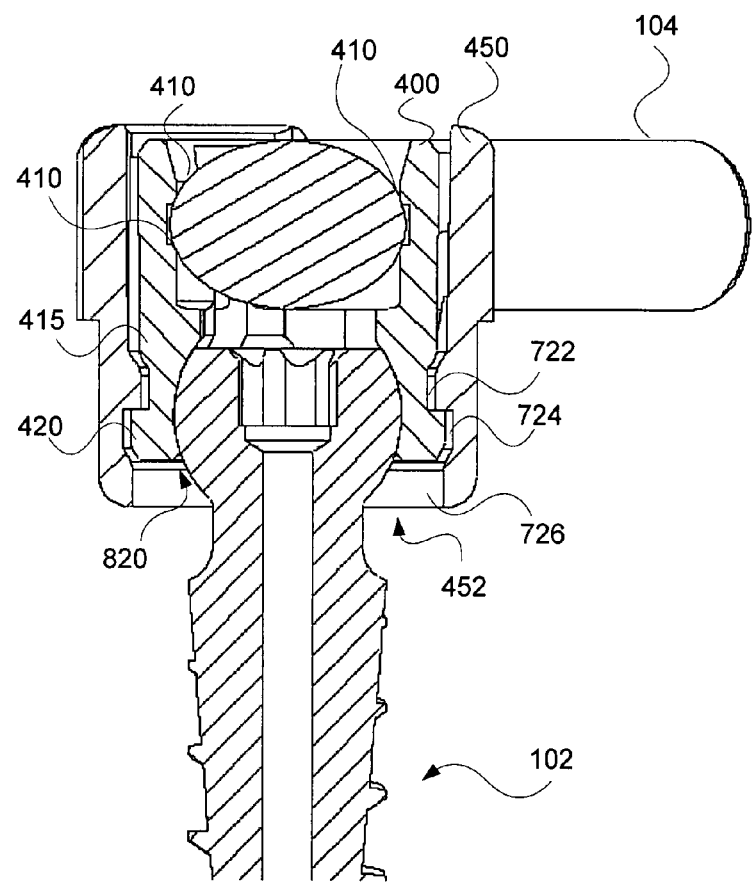
Figure 14A:
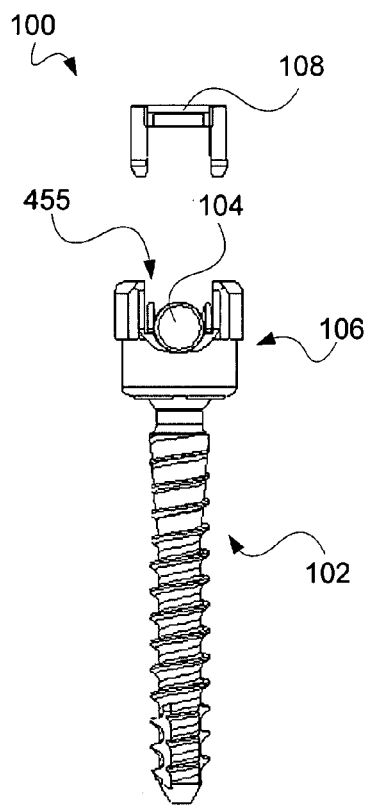
FIGS. 14A and 14B are an axial view and a cross-sectional side view, respectively, of the components of a low top pedicle screw system during provisional lock of the tulip assembly with respect to the pedicle screw, according to one exemplary embodiment.
Figure 14B:
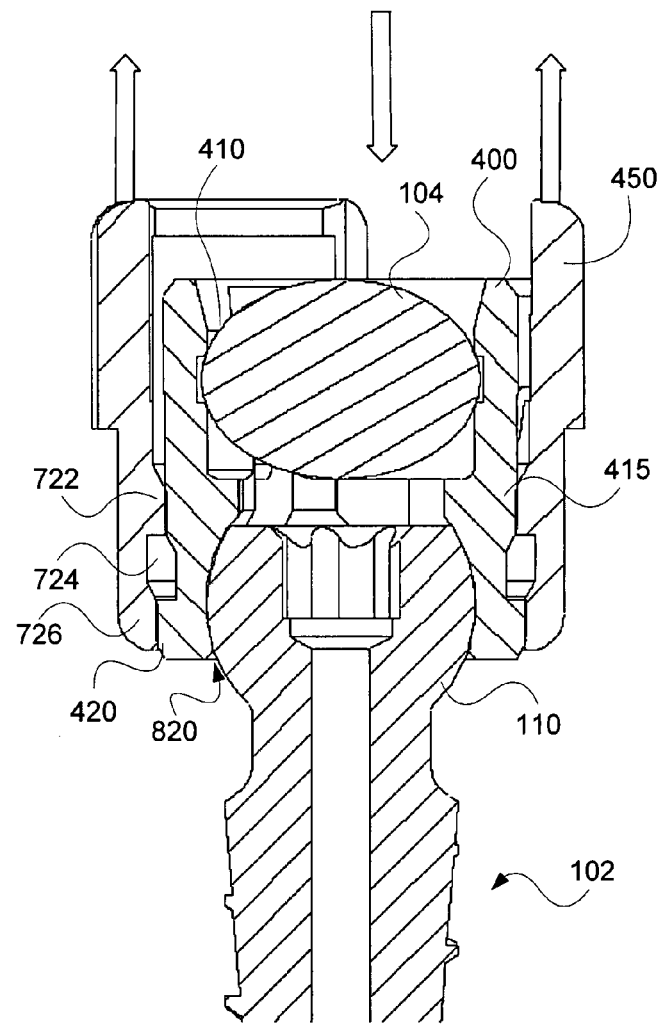

With the tulip assembly snapped over the head of the pedicle screw, a rod (104) may be inserted into the rod recess (455) of the tulip (step 1020). According to one exemplary embodiment, the rod (104) can be snapped into the inner tulip member (400) either before or after provisional locking of the tulip assembly (106). As illustrated in FIGS. 13A and 13B, both the tulip body (450) and the inner tulip member (400) are aligned to receive the rod (104). According to one exemplary embodiment, the rod recess (455) and the inner tulip member (400) are specifically sized to receive the rod (104) without significant interference. Specifically, the rod retention protrusions (800) are positioned substantially parallel with the rod recess (455) such that a clear channel to receive the rod (104) is established. During insertion of the rod to the tulip assembly (106), the rod retention protrusions (800) may expand to receive the rod (104). Once the rod (104) is received, the rod engagement members (410) establish the known points of contact on the rod. This is advantageous because it allows the frictional contact points on the rod (104) to be distributed about the perimeter of the rod, rather than having unknown, focused, or uneven points of contact. It will be understood that the tulip assembly (106) may be fixed to the pedicle screw (102) at various stages of the present exemplary installation of the pedicle screw system (100). In one exemplary embodiment, the tulip assembly (106) is fixed onto the pedicle screw (102) before the rod (104) is fixed or locked into the tulip assembly. In another embodiment, the tulip assembly (106) is fixed onto the pedicle screw (102) contemporaneously as the rod (104) is fixed or locked into the tulip assembly. For ease of explanation, the present method will continue to be described according to the exemplary method illustrated in FIG. 10.

With the rod (104) inserted in the tulip assembly (step 1030; FIG. 10), position of the tulip assembly may be oriented as desired relative to the pedicle screw (step 1030). Specifically, when the desired orientation is established, the tulip assembly position relative to the pedicle screw may be provisionally locked by positioning the inner tulip member relative to the tulip body (450). Provisional lock can be obtained by either pulling up on the tulip body (450) and/or pushing down on either the rod (104) or the inner tulip member (400), as illustrated by the arrows in FIGS. 14A and 14B. The provisional lock is obtained by the interference fit between the proximal seating feature (415) and the distal seating feature (420) of the inner tulip member (400) and the proximal annular compression feature (722) and the distal annular compression feature (726) of the tulip body (450), respectively. When the mating features are engaged, the head receiving orifice (820) is compressed about the head portion (110) of the pedicle screw (102).

It is understood that the relative angular position of a first tulip assembly (106) to a first pedicle screw (102) may be different from the relative orientation of other pedicle screw systems (100; FIG. 1) located elsewhere on a patient's spine. In general, the relative, angular position of the tulip assembly (106; FIG. 1) to the pedicle screw (102) allows the surgeon to selectively and independently orient and manipulate the tulip assemblies (106) of each pedicle screw system (100; FIG. 1) installed into the patient to achieve and/or optimize the goals of the surgical procedure, which may involve compressing, expanding, distracting, rotating, reinforcing, and/or otherwise correcting an alignment of at least a portion of a patient's spine. According to one exemplary embodiment, when the proximal seating feature (415) and the distal seating feature (420) of the inner tulip member (400) are engaged with the proximal annular compression feature (722) and the distal annular compression feature (726) of the tulip body (450), respectively, the frictional force exerted on the head portion (110) of the pedicle screw (102) is maintained, provisionally locking the tulip position.

Figure 15A:
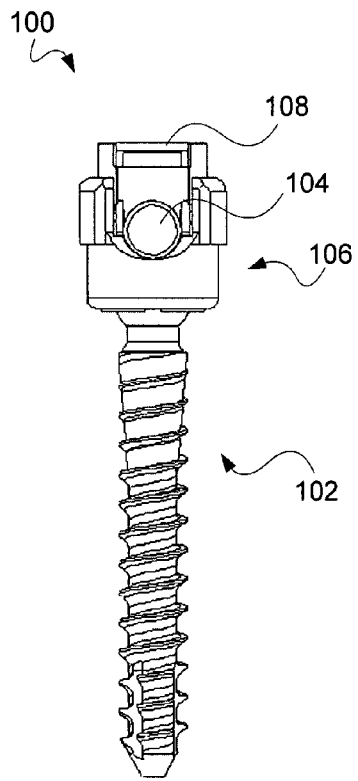
FIGS. 15A and 15B are an axial view and a cross-sectional side view, respectively, of the components of a low top pedicle screw system as a compression cap is snapped into place, according to one exemplary embodiment.
Figure 15B:
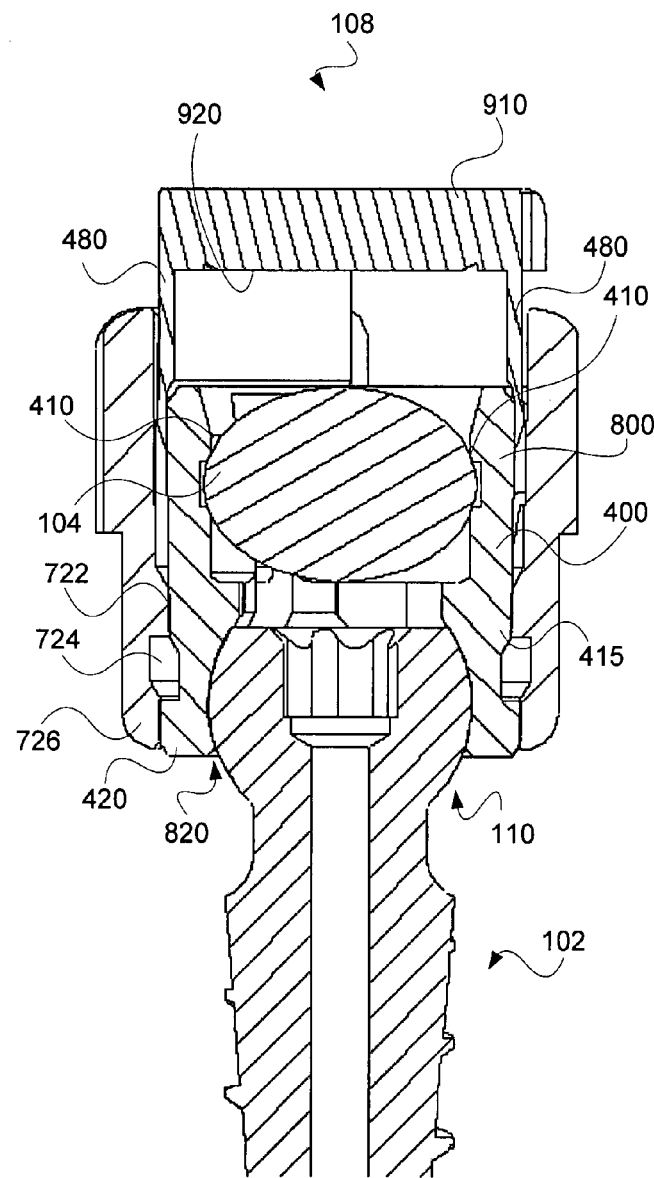

With the tulip position relative to the pedicle screw established due to the positioning of the inner tulip member (400), the compression cap (108) may be snapped into the assembly to retain the rod (step 1050). As illustrated in FIGS. 15A and 15B, the compression cap (108) is snapped into the tulip (106) but is not fully seated. According to one exemplary embodiment, the partial insertion of the compression cap (108) fills in the gap between the rod retention protrusion (800) of the inner tulip member (400) on the sides of the rod and the tulip body (450), preventing the inner tulip member from expanding around the rod (104). Consequently, the rod (104) is retained within the inner tulip member (104) and the tulip body (450) by an increased pressure or frictional force being applied at the interface between the rod engagement members (410) and the rod (104).

Figure 16A:
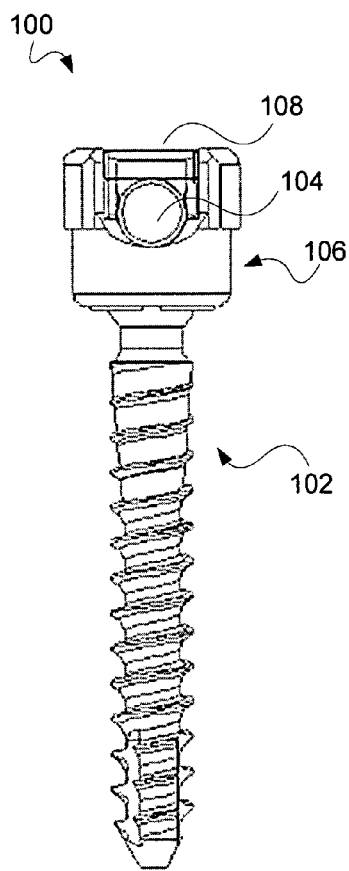
FIGS. 16A and 16B are an axial view and a cross-sectional side view, respectively, of the components of a low top pedicle screw system in a fully assembled position, according to one exemplary embodiment.
Figure 16B:
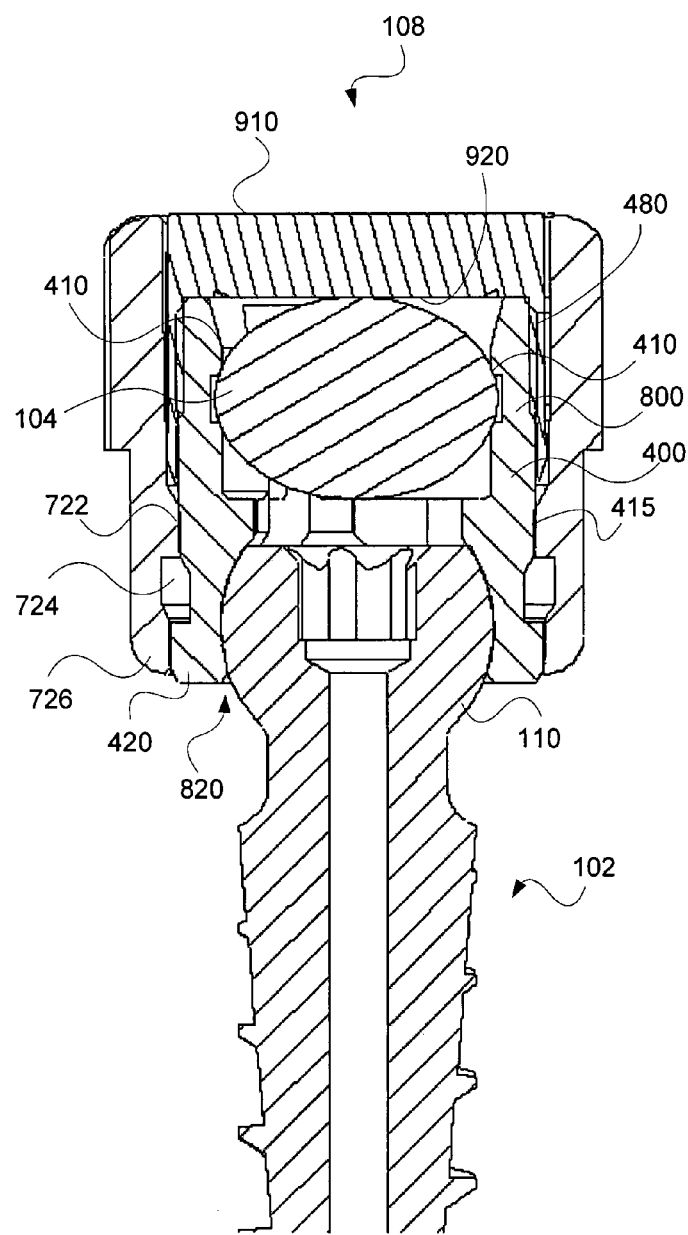

When the positioning of the all of the related components is confirmed, a complete insertion of the compression cap (108) may be performed for a final lock of the rod (step 1060). Particularly, as illustrated in FIGS. 16A and 16B, according to one exemplary embodiment, completely seating the compression cap (108) compresses the rod retention protrusions (800) of the inner tulip member (400) to grip the rod (104). Additionally, according to one exemplary embodiment, the insertion of the compression cap (108) prevents the tulip body (450) from splaying open under operative and post-operative dynamic and static loading, for example. Splaying is prevented due to the increased material that is coupled up and over the rod (104) by the compression cap (108), compared to traditional pedicle screw assemblies.

As illustrated in the exemplary embodiment of FIGS. 16A and 16B, when in the final lock position, the rod (104) is forced into substantially full engagement with the inner tulip member (400) and further downward translation is prevented by the rod stop (710) of the tulip body (450). Consequently, the resistive force exerted against the rod (104) increases the frictional resistance provided by the rod engagement members (410) to prevent the rod from slideably translating within the tulip assembly (106). According to one exemplary embodiment, the insertion of the compression cap (108) may be performed by inserting an instrument over the compression cap and forcing it downward into the assembly.

During operation, the present exemplary pedicle screw system as described, but not limited to the embodiments herein, is designed for fixation of bone material and/or bone segments during a surgical procedure, such as fusing spinal segments in which MIS techniques are employed. For example, according to one exemplary embodiment, the pedicle screw system is inserted into the pedicles of a patient's spine and then interconnected with rods to provide support to the spine to allow for post-operative fusion of the spinal segments. While the pedicle screw can be inserted with the tulip assembly coupled with the pedicle screw, one embodiment for the installation of the pedicle screw system includes inserting the pedicle screw into the bone and subsequently coupling the tulip assembly to the pedicle screw, where such an approach has advantages over currently known pedicle screw system assemblies and/or installations.

In addition, according to a number of exemplary embodiments, various structural features of the pedicle screw system as described, but not limited to the embodiments herein, may provide other advantages over existing pedicle screw systems. First, the pedicle screw may be inserted into the bone of a patient without the presence of the tulip assembly or rod, which permits the surgeon to place the screw and then perform subsequent inter-body work without having to work around the tulip assembly or the rod. Second, the tulip assembly includes a mechanism for capturing the rod that eliminates problems associated with conventional pedicle screws, such as cross-threading, because the exemplary pedicle screw systems disclosed herein do not use any threads to couple the tulip assembly to the pedicle screw or to capture and lock the rod into the tulip assembly. Third, the interface between the head portion of the pedicle screw and the tulip assembly provide an initial lock, which allows the angle of the tulip assembly to be set or fixed with respect to the pedicle screw before insertion of the rod and/or before the rod is captured in the tulip assembly. With this type of pedicle screw system, the surgeon has the ability to check and even double check the placement, angle, and/or orientation regarding aspects of the pedicle screw system to facilitate, and even optimize, the compression, distraction, and/or other manipulation of the spinal segments. Further, the present exemplary pedicle screw system accommodates the new MIS techniques being applied to spinal operations.

One possible post-operative advantage of the present exemplary pedicle screw system is that the cooperation and interaction of the inner tulip member (400) with the compression cap (108) substantially reduces, and most likely prevents, the known problem of tulip splaying. Tulip splaying is generally regarded as a post-operative problem caused by a stressed rod forcing open portions of the tulip body, which eventually leads to the disassembly and likely failure of the pedicle screw system within the patient. Yet another post-operative advantage of the pedicle screw systems is that unlike existing rod-coupling members or constructs, the exemplary tulip assemblies described herein have a smaller size envelope (e.g., less bulky, lower profile, and/or more compact shape) and are easier to place onto the pedicle screw, when compared to traditional tulip assemblies. The smaller size and ease of installation may reduce trauma to the soft-tissue regions in the vicinity of the surgical site, which in turn generally allows for a quicker recovery by the patient. According to aspects described herein, and as appended by the claims, the present exemplary pedicle screw systems permit insertion of the pedicle screw without the tulip assembly coupled thereto, locking the tulip assembly onto the pedicle screw, and subsequently capturing and locking the rod into the tulip assembly.

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What is claimed is:

1. A tulip assembly configured to be coupled to a head of a bone fixation device comprising:
    an inner tulip member including a lower portion configured to be coupled to the head of said bone fixation device and an upper rod-receiving portion including at least one flexible protrusion extending upwardly from said lower portion;
    an outer tulip member having an interior space and a central axis extending therethrough with the interior space being sized and configured to axially receive the inner tulip member and compressibly lock said lower portion of said inner tulip member on said bone fixation device; and
    a rod locking member configured for axial insertion to fit in a lateral space between the outer tulip member and the flexible protrusion and to shift said flexible protrusion in a lateral direction generally orthogonal to the central axis against the rod to securely lock said rod in the upper receiving portion of the inner tulip member.

2. The tulip assembly of claim 1, wherein said flexible protrusion comprises at least one rod engagement portion extending therefrom so that the flexible protrusion contacts the rod at one or more points about a circumference of the rod.

3. The tulip assembly of claim 1, wherein the interior space of the outer tulip member contains a wide interior portion and a narrow interior portion, the wide interior portion sized to allow expansion of the lower portion of the inner tulip member and the narrow portion sized to compress the lower portion of the inner tulip member.

4. The tulip assembly of claim 1, further comprising:
    at least one radial protrusion disposed on an outer surface of said lower portion of said inner tulip member;
    and at least one radial recess disposed on an internal wall of said outer tulip member;
    wherein said at least one radial protrusion is configured to be shifted into and out of said radial recess, and wherein the inner tulip member is in an uncompressed state when the radial protrusion is positioned in the radial recess.

5. The tulip assembly of claim 4, further comprising:
    at least one annular compression surface disposed on an internal wall of said outer tulip member;
    wherein shifting said at least one radial protrusion into engagement with said at least one annular compression surface compresses the lower portion of the inner tulip member.

6. The tulip assembly of claim 1, wherein said rod locking member is configured to be linearly inserted between said flexible protrusion and said outer tulip member.

7. The tulip assembly of claim 1, wherein said inner tulip member and said outer tulip member are configured to provisionally lock an angular orientation of said tulip assembly relative to said bone fixation device independent of said rod locking member.

8. A tulip assembly configured to be coupled to a head of a bone fixation device comprising:
    an inner tulip member including a lower portion configured to be coupled to the head of said bone fixation device and an upper rod-receiving portion including at least one flexible protrusion extending from said lower portion;
    an outer tulip member having an interior space sized and configured to axially receive the inner tulip member and compressibly lock said lower portion of said inner tulip member on said bone fixation device; and
    a rod locking member configured for insertion between the outer tulip member and the flexible protrusion and to shift said flexible protrusion against the rod to securely lock said rod in the upper receiving portion of the inner tulip member, wherein said inner tulip member further defines at least one expansion gap that extends from said lower portion into said flexible protrusion.

9. The tulip assembly of claim 8, further comprising a head receiving orifice defined by said lower portion of said inner tulip member, wherein the at least one expansion gap is configured to allow said head receiving orifice to expand during reception of said head of said bone fixation device.

10. A tulip assembly configured to be coupled to a head of a bone fixation device comprising:
    an inner tulip member including a lower portion configured to be coupled to the head of said bone fixation device and an upper portion including a plurality of flexible protrusions extending upwardly from said lower portion, said plurality of flexible protrusions each including at least one ridge configured to engage and retain said rod;
    an outer tulip member having an internal space, a central axis extending through the internal space, and an internal surface extending about the internal space, the outer tulip member being axially shiftable between a first position and a second position, so that with said outer tulip member in the first position the outer tulip is configured to enable radial expansion of said lower portion of said inner tulip member in a radial direction generally orthogonal to the central axis and with said outer tulip member in said second position the outer tulip is configured to compressibly lock said lower portion of said inner member onto said bone fixation device in the radial direction; and
    a cap including a top portion and at least one locking portion extending down from said top, said at least one locking portion being configured for linear insertion to fit in a radial space between the inner and outer tulip members to shift said flexible protrusions in the radial direction to securely lock said rod.

11. The tulip assembly of claim 10, further comprising:
    at least one annular protrusion disposed on an outer surface of said lower portion of said inner tulip member; and
    at least one annular recess disposed on an internal wall of said outer tulip member;
    wherein said at least one annular protrusion is located in said at least one annular recess of said outer tulip member in the first position thereof.

12. The tulip assembly of claim 11, wherein the outer tulip member includes an inner space and at least one annular internal wall portion that extends radially inward into the inner space for engaging with said at least one annular protrusion of said inner tulip member in said second position of said outer tulip member to compress the inner tulip member.

13. The tulip assembly of claim 10, wherein the outer tulip member has an inner space and an uppermost portion, with the tulip members being sized so that with the outer tulip member in the second position the inner tulip member is in the inner space of the outer tulip member and does not extend beyond the uppermost portion thereof, and the top portion of said cap has a generally planar configuration so that with the cap locking portion inserted between the outer and inner tulip members to lock the rod, the cap planar top portion extends across the inner tulip member and does not extend beyond the uppermost portion of the outer tulip member.

14. The tulip assembly of claim 10, wherein said inner tulip member and said locking portion of the outer tulip member are configured to lock an angular orientation of said tulip assembly relative to said bone fixation device independent of said cap.

15. The tulip assembly of claim 10, the outer tulip having an inner space with a first annularly recessed portion and a second locking portion, the locking portion being narrower than the recessed portion and located below said recessed portion.

16. A tulip assembly configured to be coupled to a head of a bone fixation device comprising:
 an inner tulip member including a lower portion configured to be coupled to the head of said bone fixation device and an upper portion including a plurality of flexible protrusions extending from said lower portion, said plurality of flexible protrusions each including at least one ridge configured to engage and retain said rod;
 an outer tulip member including a first position and a second position, so that with said outer tulip member in the first position the outer tulip is configured to enable radial expansion of said lower portion of said inner tulip member and with said outer tulip member in said second position the outer tulip is configured to compressibly lock said lower portion of said inner member onto said bone fixation device; and
 a cap including a top portion and at least one locking portion extending down from said top, said at least one locking portion being configured for linear insertion between the inner and outer tulip members to shift said flexible protrusions to securely lock said rod;
 wherein said lower portion of said inner tulip member further defines a plurality of expansion gaps configured to allow said bone fixation device to snap-lock therein.

17. A tulip assembly configured to be coupled to a head of a bone fixation device comprising:
 an inner tulip member including a lower portion configured to be coupled to the head of said bone fixation device and an upper portion including a plurality of flexible protrusions extending upwardly from said lower portion, said plurality of flexible protrusions each including at least one ridge configured to engage and retain said rod;
 an outer tulip member having an internal space, a central axis extending through the internal space, and an internal surface extending about the internal space, the outer tulip member axially shiftable between a first position and a second position, so that with said outer tulip member in the first position the outer tulip is configured to enable radial expansion of said lower portion of said inner tulip member in a radial direction generally orthogonal to the central axis and with said outer tulip member in said second position the outer tulip is configured to compressibly lock said lower portion of said inner member onto said bone fixation device in the radial direction; and
 a cap including a top portion and at least one locking portion extending down from said top, said at least one locking portion being configured for linear insertion to fit in a radial space between the inner and outer tulip members to shift said flexible in the radial direction protrusions to securely lock said rod;
 wherein said inner tulip member further defines at least one expansion gap that extends from said lower portion into said flexible protrusion.

18. A method of fixing a coupling assembly to a spinal rod and an anchor member, the method comprising:
 attaching the anchor member to a bone;
 positioning an outer member within an inner member and then expanding at least a portion of the inner member to receive a head portion of said anchor member to allow the inner and outer members to be connected to the head portion after the anchor member has been attached to the bone;
 fixing an angle of said inner member relative to said anchor member by shifting the outer member relative to the inner member to a predetermined anchor member head portion locked position;
 inserting a rod into the inner member; and
 inserting a rod locking member linearly between the outer and inner members to lock the rod in place relatively thereto without requiring threading of the rod locking member to the outer or inner member.

19. The method of claim 18 wherein the shifting of the outer member relative to the inner member to the predetermined anchor member head portion locked position occurs independently of the linear insertion of the rod locking member.

20. The method of claim 19, wherein inserting the rod locking member linearly into the assembly causes relative shifting between the outer member and inner member while locking the rod in place.

21. A pedicle screw for locking a rod to an anchor member secured to a vertebrae, the pedicle screw system, comprising:
 an outer member having an internal space;
 an insert member sized to fit in the outer member internal space;
 an upper portion of the insert member configured to receive the rod therein;
 a lower portion of the insert member configured to receive a head of the anchor member therein;
 an internal surface of the outer member and an external surface of the insert member configured to cooperate with each other to allow the outer member internal surface to be linearly shifted in a first linear direction along the insert member external surface to a predetermined anchor locked position to cause the insert member lower portion to shift laterally inwardly in the internal space generally orthogonal to the first linear direction for substantially fixing the anchor member head in the insert member lower portion; and
 a rod lock member having a rod locking actuator portion configured to be linearly shifted into the internal space in a second direction opposite to the first direction to a predetermined rod locked position causing the insert member upper portion to shift laterally inwardly in the internal space generally orthogonal to the linear directions to substantially fix the rod in the insert member upper portion.

22. The pedicle screw system of claim 21 wherein the outer member internal surface and insert member external surface are configured to capture the insert member in the outer member internal space prior to linearly shifting the outer member to the predetermined anchor locked position and allowing the rod to be received in the insert member upper portion to locate the rod entirely within the internal space.

23. The pedicle screw system of claim 21 wherein the outer member internal surface includes a pair of spaced annular ridges, and the insert member lower portion has a lower generally cylinder shaped cavity having a center therein so that with the outer member shifted to the predetermined anchor lock position, one of the ridges will be above the center and the other ridge will be below with the ridges engaging and pushing the lower portion inwardly for tightly gripping the anchor member head from above and below a center point thereof.

24. The pedicle screw system of claim 23 wherein the outer member internal surface has an annular recess between the spaced ridges, and the insert lower portion has a lower annular flange portion that is aligned with the recess to keep the insert member in the outer member internal space prior to shifting of the outer member to the predetermined anchor lock position, and the lower annular flange portion is shifted into engagement with one of the ridges with the outer member shifted to the predetermined anchor lock position.

25. The pedicle screw system of claim 21 wherein the outer member internal surface includes a lower portion having an annular recess and a pair of raised ridges that extend radially inward into the internal space with the annular recess therebetween, and the insert member lower portion has an annular recess and a pair of annular flange portions that extend radially outward with the annular recess therebetween, the insert member being held in the outer member prior to shifting of the outer member to the predetermined anchor lock position thereof by receipt of one of the raised ridges in the insert member annular recess, and with the outer member shifted to the predetermined anchor lock position the outer member recess and the insert member recess are aligned and outer member ridges are aligned and engaged with the insert member flanges to exert a radially inward force on the insert member lower portion.

26. The pedicle screw system of claim 21 wherein the rod lock member includes a pair of depending leg portions configured to fit between the outer member and insert member for shifting the upper portion thereof transversely to the second direction for substantially fixing the rod in the insert member upper portion.

27. The pedicle screw system of claim 26 wherein the insert member lower portion has a generally annular configuration and the insert member upper portion includes a pair of upstanding opposite arm portions each extending straight across the annular lower portion along chord lines thereof with the depending leg portions inserted between the outer member and insert member arm portions to push the arm portions toward each other for clamping on the rod extending therebetween.

28. The pedicle screw system of claim 26 wherein the outer member includes a lower annular portion and a pair of upstanding opposite wall portions, and the leg portions of the rod lock member are sized to be wedge fit between the upstanding wall portions and the insert member upper portion to be shifted for substantially fixing the rod therein.

* * * * *